United States Patent [19]

Turconi et al.

[11] Patent Number: 5,223,511
[45] Date of Patent: Jun. 29, 1993

[54] BENZIMIDAZOLINE-2-OXO-1-CARBOXY-LIC ACID COMPOUNDS USEFUL AS 5-HT RECEPTOR ANTAGONISTS

[75] Inventors: Marco Turconi, Voghera; Arturo Donetti, Milan; Ernesto Montagna, San Giuliano Milanese; Massimo Nicola, Pavia; Annamaria Uberti, Milan; Rosamaria Micheletti, Milan; Antonio Giachetti, Milan, all of Italy

[73] Assignee: Boehringer Ingelheim Italia S.p.A., Florence, Italy

[21] Appl. No.: 845,891

[22] Filed: Mar. 4, 1992

Related U.S. Application Data

[63] Continuation-in-part of Ser. No. 768,497, Sep. 30, 1991, abandoned, which is a continuation of Ser. No. 552,353, Jul. 12, 1990, abandoned, which is a continuation of Ser. No. 243,949, Sep. 13, 1988, abandoned.

[30] Foreign Application Priority Data

Sep. 23, 1987 [IT] Italy .................. 21997 A/87

[51] Int. Cl.$^5$ .................. C07D 451/12; A61K 31/46
[52] U.S. Cl. .................. 514/304; 546/126
[58] Field of Search .................. 546/126; 514/304

[56] References Cited

U.S. PATENT DOCUMENTS 4,871,744 10/1989 King et al. .................. 546/126

FOREIGN PATENT DOCUMENTS 0223385 5/1987 European Pat. Off. .................. 546/126

*Primary Examiner*—C. Warren Ivy
*Assistant Examiner*—Zinna N. Davis
*Attorney, Agent, or Firm*—David E. Frankhouser; Alan R. Stempel; Mary-Ellen M. Timbers

[57] ABSTRACT

New pharmacologically active benzimidazoline-2-oxo-1-carboxylic acid derivatives which are 5-HT receptor antagonists useful as antiemetic agents and as gastric prokinetic agents of the following formula:

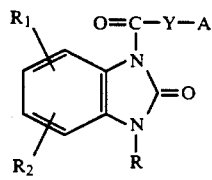

(I)

wherein R is hydrogen, $C_{1-6}$ alkyl, $C_{2-6}$ alkenyl or $C_{2-6}$ alkynyl; $R_1$ is hydrogen; $R_2$ is hydrogen, halogen or $C_{1-6}$ alkoxy; Y is oxygen or $N-R_3$ in which $R_3$ is hydrogen; A is a group selected from:

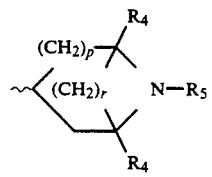

(a)

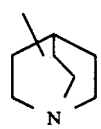

(b)

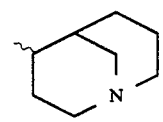

(c)

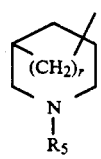

(d)

wherein p is 1; r is 0, 2 or 3: $R_4$ is hydrogen; $R_5$ is hydrogen, $C_{1-6}$ alkyl, or $R_5$ is a group of the formula $-CR_6=N-R_7$ wherein $R_6$ is hydrogen, $C_{1-4}$ alkyl or amino and $R_7$ is hydrogen or $C_{1-6}$ alkyl; or a pharmaceutically acceptable acid addition salt thereof.

The processes for the preparation of the compounds of formula (I) as well as pharmaceutical compositions containing them are also described.

9 Claims, No Drawings

BENZIMIDAZOLINE-2-OXO-1-CARBOXYLIC ACID COMPOUNDS USEFUL AS 5-HT RECEPTOR ANTAGONISTS

RELATED APPLICATIONS

This is a continuation-in-part of application Ser. No. 768,497, filed Sep. 30, 1991, now abandoned, which is a continuation of application Ser. No. 552,353, filed Jul. 12, 1990, now abandoned, which is a continuation of application Ser. No. 243,949, filed Sep. 13, 1988, now abandoned.

FIELD OF THE INVENTION

The present invention relates to novel pharmacologically active benzimidazoline-2-oxo-1-carboxylic acid derivatives, to the process for their preparation and to the pharmaceutical compositions containing them. The new compounds are 5-HT receptor antagonists useful as antiemetic agents and as gastric prokinetic agents.

BACKGROUND OF THE INVENTION

Serotonin (5-HT) is known to play a major role both in Central Nervous System (CNS) and in Peripheral Nervous System (PNS). Compounds acting as 5-HT receptor antagonists may be effectively used in the prevention or treatment of migraine, cluster headaches and trigeminal neuralgia. They may also be used in the treatment of certain CNS disorders such as anxiety and psychosis. Since 5-HT antagonists may have a beneficial role on gastrointestinal motility a further use of these compounds is in the treatment of delayed gastric emptying, and related disorders such as dyspepsia, flatulence, oesophageal reflux, peptic ulcer, constipation and irritable bowel syndrome. Very recently it has been also discovered that a number of 5-HT antagonists may be particularly useful in the treatment of chemotherapy induced nausea and emesis (J. R. Fozard-Trends in Pharmacological Sciences 8 44, 1987, and references cited therein).

DESCRIPTION OF THE INVENTION

We have now synthesized, and this is the object of the present invention, a novel class of structurally distinct compounds which exhibit a specific 5-HT receptor blocking activity which are useful in the treatment of chemotherapy and radiation induced nausea and emesis and/or of delayed gastric emptying. They are also of value in the treatment of motion sickness, arrhytnmia, migraine, cluster headaches, trigeminal neuralgia, anxiety and psychosis. Moreover they are useful in the treatment of gastrointestinal motility disorders such as gastrointestinal ipomotility and related disorders such as dyspepsia, flatulence, oesophageal reflux, peptic ulcer, constipation, irritable bowel syndrome. The compounds, object of the present invention, have the general formula (I)

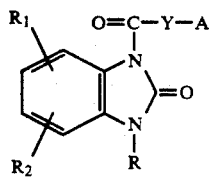
(I)

wherein R is hydrogen, $C_{1-6}$ alkyl, $C_{2-6}$ alkenyl or $C_{2-6}$ alkynyl; $R_1$ is hydrogen; $R_2$ is hydrogen, halogen, or $C_{1-6}$ alkoxy; Y is oxygen or $N-R_3$, in which $R_3$ is hydrogen; A is a group selected from:

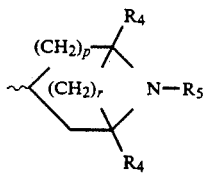 (a)

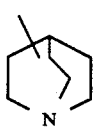 (b)

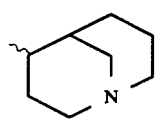 (c)

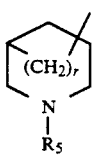 (d)

wherein p is 1; r is 0, 2 or 3; $R_4$ is hydrogen; $R_5$ is hydrogen, $C_{1-6}$ alkyl, or $R_5$ is a group of the formula $-CR_6=N-R_7$ wherein $R_6$ is hydrogen, $C_{1-4}$ alkyl or amino and $R_7$ is hydrogen or $C_{1-6}$ alkyl.

For pharmaceutical use the compounds of general formula (I) can be used in the form shown, or in the form of tautomers or as physiologically acceptable acid addition salts. The term "acid addition salts" includes salts with inorganic or organic acids. Physiologically acceptable acids used for the salification include, for example, maleic, citric, tartaric, fumaric, methansulphonic, hydrochloric, hydrobromic, idroiodic, nitric, sulphuric, phosphoric, acetic, benzoic, ascorbic acid. Physiologically acceptable salts include also quaternary derivatives of compounds of formula (I) obtained by reaction of the above compounds with compounds of formula $R_8-Q$ wherein $R_8$ is $C_{1-6}$ alkyl, phenyl $C_{1-6}$ alkyl or $C_{3-7}$ cycloalkyl $C_{1-4}$ alkyl and Q is a leaving group such as halogen, p-toluensulphonate, mesylate. Preferred $R_8$ groups are methyl, ethyl, n-propyl, isopropyl and cyclopropylmethyl. Physiologically acceptable salts also include internal salts of compounds of formula (I) such as N-oxides. The compounds of formula (I) and their physiologically acceptable salts may also exist as physiologically acceptable solvates, such as hydrates, which constitute a further aspect of the present invention. It has to be understood that the carbonyl group in position two of the general formula (I) might exist in its enol form when R is hydrogen and that there are also the tautomers of the amidino derivatives of formula (I) wherein $R_5$ is a group of formula $-CR_6=N-R_7$ and $R_6$ and $R_7$ are as hereinbefore defined. The present invention therefore includes in its scope these tautomeric forms.

Some of the compounds of formula (I) according to the present invention contain chiral or prochiral centres and thus may exist in different stereoisomeric forms including enantiomers of (+) and (−) type or mixtures of them. The present invention includes in its scope both the individual isomers and the mixtures thereof.

It has to be understood that, when mixtures of optical isomers are present, they may be separated according to the classic resolution methods based on their different physico-chemical properties, e.g. by fractional crystallization of their acid addition salts with a suitable optically active acid or by the chromatographic separation with a suitable mixture of solvents.

In the present invention the term A of formula (a) means 3-linked 8-azabicyclo [3.2.1] octane or 3-linked 9-azabicyclo [3.3.1] nonane or 2-linked 7-azabicyclo [2.2.1] heptane, 4-linked piperidine, the one of formula (b) means 3 or 4-linked 1-azabicyclo [2.2.2] octane, the one of formula (c) means 4-linked 1-azabicyclo [3.3.1] nonane and the one of formula (d) means 5-linked 2-azabicyclo [2.2.2] octane. The term halogen means fluorine, chlorine, bromine or iodine. It has also to be understood that in compounds of formula (I) the azabicyclic moieties of group A may be endo or exo substitued.

Compounds of formula (I) containing the pure endo or exo moieties may be prepared starting from the appropriate precursors or by separating mixtures of the endo or exo isomers not stereospecifically synthesized, by conventional methods such as e.g.: chromatography.

Preferred compounds of formula I, based upon their activity as 5-HT receptor blocking agents, are those wherein:

A is endo-8-methyl-8-azabicyclo[3-2-1]oct-3-yl, $R_1$ and $R_2$ are H, R is H, $C_{1-6}$ alkyl, $C_{2-6}$ alkenyl or $C_{2-6}$ alkynyl and Y is oxygen or NH;

A is 1-azabicyclo [2.2.2] oct-3-yl, $R_1$ and $R_2$ are H, R is H, $C_{1-6}$ alkyl, $C_{2-6}$ alkenyl or $C_{2-6}$ alkynyl and Y is oxygen or NH;

A is endo-9-methyl-9-azabicyclo[3.3.1]non-3-yl, $R_1$ and $R_2$ are H, R is H, $C_{1-6}$ alkyl, $C_{2-6}$ alkenyl or $C_{2-6}$ alkynyl and Y is oxygen or NH; or, A is endo-1-azabicyclo [3.3.1]non-4-yl, $R_1$ and $R_2$ are H, R is H, $C_{1-6}$ alkyl, $C_{2-6}$ alkenyl or $C_{2-6}$ alkynyl and Y is oxygen or NH.

The compounds of general formula (I) when R is H may be prepared by reacting a compound of general formula (II)

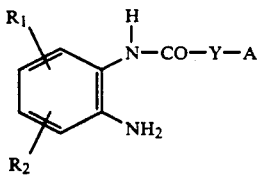 (II)

wherein $R_1$, $R_2$, Y and A are as hereinbefore defined, with a reactive carbonyl derivative of formula (III)

 (III)

wherein X and $X^1$ are leaving groups which may each be, for example, halogen, halogenated alkoxy, alkoxy or a heterocycle. Preferred groups are chlorine, trichloromethoxy, methoxy, ethoxy or imidazolyl. The reaction may be conveniently carried out in aprotic solvents such as benzene, toluene, ethylacetate, acetonitrile, tetrahydro-furan, methylene chloride, chloroform, carbon-tetrachloride or dimethyl-formamide at a temperature ranging from 0° to 100° C., preferably at 5° C., at room temperature or at the boiling point of the solvent of choice. The presence of an acid acceptor such as triethylamine may be beneficial in some instances. Compounds of general formula (II), used as starting materials in the above mentioned process, may be prepared by reducing a compound of formula (IV)

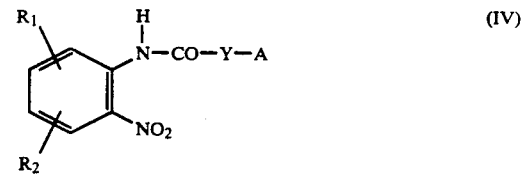 (IV)

wherein $R_1$, $R_2$, Y and A are as hereinbefore defined, with hydrogen or a hydrogen donor such as ammonium formate, cyclohexene, cyclohexadiene, or hydrazine. The reduction is preferably carried out with hydrogen in the presence of a suitable catalyst, preferably 5% or 10% Pd/C or Raney nickel in the presence of a suitable solvent such as methanol, ethanol, toluene, water or a mixture of them. The same reduction may be conveniently carried out with iron in acidic medium or in the presence of $FeCl_3$, with Zn in acetic or hydrochloric acid, with $SnCl_2$ in hydrochloric acid or with other reducing agents such as titanium trichloride, ferrous sulphate, hydrogen sulphide or its salts, sodium hydrosulphite.

Compounds of general formula (IV) may be prepared by reacting a compound of general formula (V)

 (V)

wherein $R_1$ and $R_2$ are as hereinbefore defined, with a reactive intermediate of general formula (VI)

 (VI)

wherein X, Y and A are as hereinbefore defined. The reaction is carried out in an aprotic solvent such as tetrahydrofuran, acetonitrile, chloroform, toluene, chlorobenzene or without solvents, and optionally in the presence of an acid acceptor, preferably in pyridine at a temperature ranging from 20° to 100° C. preferably at 20° or at 80° C.

Compounds of general formula (V) are either commercially available or may be conveniently prepared according to known procedures. For example, 5-fluoro-2-nitro-aniline is prepared according to Courtin Helv. Chim. Acta 65, 546 (1982), 5-methoxy-2-nitro-aniline is prepared according to Morrin Achesan R et al. J. Chem. Soc., Perkin Trans 1, 1117 (1978). Compounds of general formula (VI) may be prepared by reacting a compound of general formula (VII)

 (VII)

wherein A and Y are as hereinbefore defined, preferably Y is an oxygen atom, with a compound of formula (III), wherein X and $X^1$ are as hereinbefore defined, preferably halogen and halogenated alkoxy. The reaction is carried out in aprotic solvents such as tetrahydrofuran, acetonitrile, methylene chloride or chloroform at a temperature between 10° C. and the boiling point of the solvent of choice, preferably at room temperature. Compounds of general formula (VI) are preferably isolated as hydrochloride salts.

Compounds of general formula (VII) are either commercially available or may be prepared according to known procedures, for example, endo-9-methyl-9-azabicyclo [3.3.1]nonan-3-ol is prepared according to C. L. Zirkle et al. J. Org. Chem 26, 395 (1961), endo-8-phenyl-methyl-8. azabicyclo[3.2.1]octan-3-ol is prepared according to Nador et al. Arzeneim Forsch 12, 305 (1962)

The compounds of general formula (I), wherein $R_1$ and $R_2$ are both hydrogen atoms and R, Y and A are as hereinbefore defined, may conveniently be obtained by reacting a compound of formula (VIII)

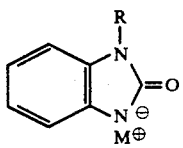

(VIII)

wherein M is a metal atom, such as sodium, potassium or lithium, preferably sodium with a compound of formula (VI). The reaction is preferably carried out in a polar aprotic solvent, such as dimethyl formamide or tetrahydrofuran at a temperature ranging from 0° to 100° C., preferably at room temperature.

Compound (VIII) is generated "in situ" from the corresponding hydrogen compounds by means of sodium, potassium, sodium hydride, potassium hydride, potassium tert-butylate, buthyllithium, lithium diisopropylamide, preferably sodium hydride.

Compounds which can be used to prepare the hydrogen compounds of formula (VIII) are either commercially available or may be prepared according to Z. Eckstein et al. J. Chem. Engineering Data 28, 279 (1983), or the references cited therein.

The compounds of general formula (I), wherein $R_1$ and $R_2$ are both hydrogen atoms R, Y and A are as hereinbefore defined, may be also prepared by reacting a reactive compound of general formula (IX)

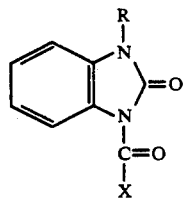

(IX)

wherein R and X are as hereinbefore defined, with a compound of formula (X)

Z-Y-A (X)

wherein Z is a hydrogen atom, a metal preferably Li, Na or K, Y and A are as hereinbefore defined. The reaction is carried out in an aprotic solvent such as tetrahydrofuran, chloroform, acetonitrile, o-dichlorobenzene and optionally in the presence of an acid acceptor such as pyridine or triethylamine, preferably pyridine, at a temperature ranging from 0° to 200° C., preferably between 20° and 160° C. Compounds of general formula (IX), used as starting materials in the above mentioned process, wherein R is hereinbefore defined and X is chlorine, may be prepared according to the method described by W. H. W. Lunn U.S. Pat. No. 4,061,861. Alternatively the same compounds may be prepared by reacting a compound of general formula (XI)

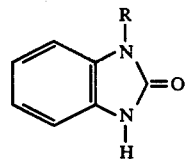

(XI)

wherein R is an hereinbefore defined, with a compound of general formula (III), wherein X and $X^1$ are as hereinbefore defined, preferably they are halogen and halogenated alkoxy. The reaction is preferably carried out in an inert solvent, such as tetrahydrofuran, dioxane or dichlorobenzene optionally in the presence of charcoal at temperature between 50° C. and 150° C., preferably at the boiling point of the solvent. Compounds of general formula (XI) are either commercially available or they may be prepared according to Z. Eckstein et al. J. Chem. Engineering Data 28, 279 (1983).

Compounds of general formula (X), used as starting materials in the above mentioned process, wherein Z is a metal atom as hereinbefore defined, may be conveniently prepared by reacting a compound of general formula (VII)

H-Y-A (VII)

wherein Y and A are as hereinbefore defined, with a metal, a metal hydride or a strong base such as, for example, sodium hydride, potassium hydride, metallic sodium or potassium, potassium t-butylate, butyl lithium, lithium diisopropylamide, preferably sodium hydride or butyl lithium in an aprotic solvent such as tetrahydrofuran, diethyl ether or dimethylformamide. The reaction is preferably carried out at a temperature between −78° C. to room temperature. Compounds of formula (VII) are either commercially available or may be prepared according to known procedures (c.f., for example, C. L. Zirkle et al. J. Org. Chem. 26, 395 (1961); J. Med. Chem. 16, 853 (1973); S. Archer J. Am. Chem. Soc. 79, 41 (1957); Chemical Abstract 94, 65477 (1981); European Patent Application 94.742 (1983); E. F. Elslager J. Med. Chem. 17, 75 (1974); G. Kraiss et al. Tetrahedron Lett. 12, 57 (1971); P. Dorstert et al. Eur. J. Med. Chem. 19, 105 (1984). It has to be understood that compounds of general formula (I) containing an R, $R_1$, $R_2$, $R_3$ and $R_5$ group which may give rise to another R, $R_1$, $R_2$, $R_3$ and $R_5$ group, are useful novel intermediates. Some of these transformations may also occur in the intermediates for compounds of general formula (I). Some examples of such conversions, which obviously are not exhaustive of all possibilities, are:

1) a nitro group may be transformed into an amino group by reduction;
2) an amino group may be transformed into a $C_{1-6}$ acylamino group by acylation with a suitable carboxylic acid derivative;
3) an amino group may be transformed into a $C_{1-4}$ alkyl N-mono or di-substituted group by alkylation;

4) an amino group may be transformed into a $C_{1-6}$ alkoxy carbonyl amino group by reaction with a suitable reactive $C_{1-6}$ alkyl carbonic acid monoester derivative;

5) a carboxyl group may be transformed into a $C_{1-6}$ alkoxy carbonyl group, or into a carbamoyl group optionally $C_{1-4}$ alkyl N-mono or di-substituted by reaction of a suitable reactive carboxylic acid derivative with appropriate alcohols and amines;

6) a carbamoyl group may be transformed into a cyano group by dehydration;

7) a $C_{1-6}$ alkyl thio or a $C_{1-6}$ alkyl suphinyl group may be transformed into a $C_{1-6}$ alkyl sulphinyl or a $C_{1-6}$ alkylsuphonyl group by oxidation;

8) an aromatic hydrogen group may be transformed into a nitro group by nitration;

9) a hydrogen group may be transformed into a halogen group by halogenation;

10) a secondary amide group, optionally conjugated with other carboxamidic moieties, may be transformed into a $C_{1-6}$ N-alkyl tertiary amide group by alkylation;

11) a secondary amino group may be transformed into an amidino derivative by reaction with appropriate reactive compounds such as e.g. ethyl formimidate, ethyl acetimidate or cyanamide;

12) a tertiary amino group may be transformed into a quaternary ammonium derivative by reaction with a suitable alkylating agent such as methyl bromide or methyl iodide;

13) a tertiary amidic group optionally conjugated with other carboxamidic moieties may be transformed into a secondary amidic group by removing an optionally $C_{1-6}$ alkoxy substituted benzyl.

These transformations are well known to any expert of the branch.

The compounds of general formula (I) prepared according to the process as above described may optionally be converted with inorganic or organic acids into the corresponding physiologically compatible acid addition salts, for example, by conventional methods such as by reacting the compound, as base, with a solution of the corresponding acid in a suitable solvent. Particularly preferred acids include for example hydrochloric, hydrobromic, sulphuric, acetic, citric, tartaric acids.

Particularly preferred compounds, according to the present invention are the following:

N-(1-azabicyclo[2.2.2]oct-3-yl)-2,3-dihydro-2-oxo-1H-benzimidazole-1-carboxamide (Compound 28).

N-(endo-9-methyl-9-azabicyclo[3.3.1]non-3-yl)-3-methyl-2,3-dihydro-2-oxo-1H-benzimidazole-1-carboxamide (Compound 31).

N-(endo-8-methyl-8-azabicyclo[3.2.1]oct-3-yl)-2,3-dihydro-2-oxo-1H-benzimidazole-1-carboxamide (Compound 26).

N-(endo-9-methyl-9-azabicyclo[3.3.1]non-3-yl)-2,3-dihydro-2-oxo-1H-benzimidazole-1-carboxamide (Compound 27).

N-(endo-8-methyl-8-azabicyclo[3.2.1]oct-3-yl)-3-methyl-2,3-dihydro-2-oxo-1H-benzimidazole-1-carboxamide (Compound 32).

2,3-dihydro-2-oxo-1H-benzimidazole-1-carboxylic acid (endo-9-methyl-9-azabicyclo[3.3.1]non-3-yl) ester (Compound 19).

N-(endo-8-methyl-8-azabicyclo[3.2.1]oct-3-yl)-2,3-dihydro-3-ethyl-2-oxo-1H-benzimidazole-1-carboxamide (Compound 45).

3-Ethyl-2,3-dihydro-2-oxo-1H-benzimidazole-1-carboxylic acid (endo-8-methyl-8-azabicyclo[3.2.1]oct-3-yl) ester (Compound 60).

2,3-dihydro-2-oxo-1H-benzimidazole-1-carboxylic acid (endo-8-amidino-8-azabicyclo[3.2.1]oct-3yl) ester (Compound 44).

As already mentioned hereinbefore the new compounds of formula (I), according to the present invention, have useful pharmacological properties owing to their ability to antagonize the physiological 5-HT effects in warm-blooded animals. Therefore the new compounds are commercially viable in the prevention and in the treatment of disorders wherein 5-HT receptors are involved such as chemotherapy or radiation induced nausea and emesis, delayed gastric emptying, psychosis, and anxiety.

The following tests show that the compounds according to the present invention have favorable characteristics in these respects.

PHARMACOLOGY

Bezold-Jarisch reflex in anaesthetized rats

Rats (250–275 g) were anaesthetized with urethane (1.25 g/kg ip.). Blood pressure was recorded from the left femoral artery by means of a pressure transducer (Statham) and heart rate was recorded by feeding a cardiotachometer with the blood pressure signal.

The Bezold-Jarisch effect was elicited by rapid bolus intravenous injection of 5-HT (20 µg/kg).

Increasing doses of antagonists were injected 5 min before 5-HT to evaluate their effect on the initial abrupt cardiac slowing and associated fall in blood pressure resulting from the reflex vagal stimulation. $ED_{50}$ values were calculated by linear regression analysis of the data expressed as percentage inhibition.

The obtained potency of the compounds, object of the present invention, is reported in the table I.

TABLE I

| Compound | Bradycardia $ED_{50}$ (µg/kg, i.v.) | Hypotension $ED_{50}$ (µg/kg, i.v.) |
|---|---|---|
| 1 | 5.4 | 5.9 |
| 19 | 3.4 | 6.8 |
| 24 | 5.7 | 7.8 |
| 25 | 12.0 | 8.5 |
| 26 | 0.3 | 0.4 |
| 27 | 0.35 | 6.5 |
| 28 | 1.0 | 1.5 |
| 31 | 0.49 | 1.97 |
| 32 | 1.7 | 2.2 |
| 37 | 3.7 | 3.9 |
| 44 | 0.0003 | 0.0004 |
| 45 | 1.7 | 1.0 |
| 47 | 1.7 | 2.2 |
| 48 | 4.7 | 6.4 |
| 50 | 6.1 | 5.8 |
| 51 | 0.4 | 1.3 |
| 52 | 0.3 | 1.1 |
| 54 | 0.6 | 2.0 |
| 56 | 1.3 | 1.4 |
| 57 | 4.0 | 3.1 |
| 60 | 3.2 | 5.2 |

Guinea pig ileum longitudinal muscle-myenteric plexus

Male guinea pigs (Dunkin Hartley, 450–550 g) were killed by cervical dislocation. A 2 cm segment of distal ileum, removed about 10 cm proximal to the caceum was suspended under 0.5 g tension in a 10 ml organ bath containing Tyrode solution (mM: NaCl 137; KCl 2.68; $CaCl_2$ 1.82; $NaHCO_3$ 5.9; $MgCl_2$ 1; $NaH_2PO_4$ 0.42; glucose 5.6) oxygenated with 95% $O_2$ 5% $CO_2$, at 37° C.

Responses were registered with an isotonic transducer on a polygraph (Basile).

Electrical field stimulation (EFS) was performed with bipolar platinum electrodes, with 0.5 msec pulses at 0.1 Hz frequency, supramaximal voltage. When contractions had stabilized, cumulative concentration-response curves were constructed for the compounds under investigation, by adding increasing concentration at 5 min intervals.

The effect of compounds of EFS evoked contractions was evaluated as percentage of the contraction height measured before addition of compounds.

The compounds, object of the present invention, strengthened the contractions induced by electrical stimulation in the guinea pig ileum in the concentration range $10^{-10}$–$10^{-8}$M, while having no effect on muscle tone.

Antiemetic Activity

Beagle dogs of both sexes (8–12 kg b.w.) were administered cisplatin (3 mg/kg) by intravenous route. Number of emetic episodes was counted during 5 hrs after cisplatin administration. 5 min before cisplatin, animals were given saline (control animals) or a dose of antagonist (treated animals) by i.v. route. In each experiment with an antagonist, protection was calculated as percentage inhibition of the number of emetic episodes in the treated animal compared to the average value obtained in the control group. Linear regression analysis was applied, and the dose reducing by 50% the number of emetic episodes in the control group ($ED_{50}$) was estimated.

The potency ($ED_{50}$, μg/kg i.v.) of tested compounds, is shown below:

| Compound 26 | 21.5 μg/kg |
| Compound 45 | 3.7 μg/kg |
| Compound 50 | 1.3 μg/kg |
| Compound 1 | 146.0 μg/kg |
| Compound 27 | 3.6 μg/kg |
| Compound 47 | 4.4 μg/kg |
| Compound 60 | 3.7 μg/kg |

Gastric Emptying Properties

This model provides evidence of a facilitation of gastrointestinal peristalsis which may be of benefit in pathological situations related to gastrointestinal ipomotility (Costall and Naylor, Scand. J. Gastroenterology 25, 769–787, 1990).

Male rats fasted for 24 hours before the experiments, were administered amberlite pellets by stomach gavage. The test drugs were administered intraperitoneally immediately after the gastric gavage. The animals were killed 60 min after pellets administration; the stomach was carefully removed and opened and the pellets remaining inside were counted. $ED_{50}$ value (i.e. the dose that reduces by 50% the number of pellets retained in the stomach of control group) and relative confidence limits (P<0.05) were calculated.

The results of the test are set in the following table:

| Compound | $ED_{50}$ μg/kg i.p. | 95% c.l. |
|---|---|---|
| 26 | 34.7 | 17.7–68.0 |
| 45 | 11.0 | 7.0–19.0 |
| 50 | 34.4 | 26.1–45.3 |
| 1 | 107.9 | 16.6–701.1 |
| 27 | 59.4 | 21.8–161.9 |
| 28 | 229.0 | 47.6–1879.4 |
| 47 | 6.4 | 2.3–17.5 |
| 48 | 3.9 | 1.2–12.9 |
| 60 | 163.2 | 92.5–288.0 |

Anxiolytic Properties

Method: light/dark exploratory test in mice.

The procedure is as described in Jones et al. (Br. J. Pharmacol. 93:985–993, 1988) and is based on the aversion of mice to wide, brightly lit areas. The apparatus is an open-topped box divided into a small and large area by a partition which has a hole at floor level. The small compartment, painted black, is illuminated with red light and the large compartment, painted white, is illuminated by white light. Control animals spend most of their time in the dark area. Animals treated with anxiolytic drugs spend a longer time in the bright area.

Results: tested compounds induced animals to spend a longer time in the bright area, as reported in the following table:

| Treatment | Dose mg/kg | Time (sec) dark | Time (sec) light |
|---|---|---|---|
| VEHICLE | — | 132 ± 48 | 48 ± 22 |
| COMPOUND 26 | 0.001 | 97 ± 33* | 84 ± 33* |
| VEHICLE | — | 109 ± 12 | 71 ± 12 |
| COMPOUND 45 | 0.001 | 50 ± 32* | 128 ± 30* |
| COMPOUND 50 | 0.01 | 58 ± 61* | 122 ± 61* |
| VEHICLE | — | 126 ± 8 | 54 ± 8 |
| COMPOUND 48 | 0.003 | 114 ± 24+ | 66 ± 24+ |
| VEHICLE | — | 125 + 11 | 55 ± 11 |
| COMPOUND 31 | 0.001 | 106 ± 5+ | 74 ± 5+ |

Values represent mean ± S.D. from 8–10 mice.
Compounds were administered i.p. 45 before testing.
Anova test: P<0.05; +trend of difference vs vehicle, not significant.

Antipsychotic properties

The chronic treatment with typical antipsychotic drugs causes a decrease in the number of spontaneously active dopaminergic neurones in the Ventral Tegmental Area of rat brain (Bunney and Grace, Life Sci. 23: 1715, 1978).

Method: the number of spontaneously active dopaminergic neurones in the Ventral Tegmental Area was detected as described by Bunney and Grace (Life Sci. 23: 1715, 1978) in rats treated for 21 days with compound 26.

Results: Compound 26 (15 μg/kg s.c., twice daily, for 21 days) significantly reduced the number of spontaneously active dopaminergic cells in the Ventral Tegmental Area:

| Treatment | Dose | Dopaminergic cells per track |
|---|---|---|
| VEHICLE | — | 1.6 ± 0.10 |
| COMPOUND 26 | 15 μg/kg s.c. twice daily for 21 days | 0.9 ± 0.06* |

Values represent means ± s.e.m. from 12–13 rats.
Student's test: *p < 0.05.

According to a further aspect of the present invention, there are provided pharmaceutical compositions comprising as active ingredient at least one compound of formula (I), as hereinbefore defined, or a physiologically compatible acid addition salt thereof in association with pharmaceutical carriers or excipients.

For pharmaceutical administration the compounds of general formula (I) and their physiologically compatible acid addition salts may be incorporated into the conventional pharmaceutical preparations in either solid or liquid form. The compositions may, for example, be presented in a form suitable for oral, rectal or parenteral administration. Preferred forms include, for example, capsules, tablets, coated tablets, ampoules, suppositories and oral drops. The active ingredient may be incorporated in excipients or carrier conventionally used in pharmaceutical compositions such as, for example, talc, gum arabic, lactose, gelatine, magnesium stearate, corn starch, aqueous or non-aqueous vehicles, polyvinylpyrrolidone, mannitol, semisynthetic gliceridies of fatty acids, sorbitol, propylene glycol, citric acid, sodium citrate. The compositions are advantageously formulated at dosage units, each dosage unit being adapted to supply a single dose of the active ingredient. Each dosage unit may conveniently contain from 50 mg to 1000 mg and preferably from 100 mg to 500 mg of the above ingredient.

The following examples illustrate some of the new compounds according to the present invention; These examples are not to be in any way considered limitative of the scope of the invention itself:

EXAMPLE 1

Endo-8-methyl-8-azabicyclo[3.2.1]octo-3-yl chloroformate hydrochloride 43 g of the endo-8-methyl-8-azabicyclo [3.2.1]octan-3-ol hydrochloride were suspended in 400 ml of acetonitrile and 62.2 g of trichloromethyl chloroformate dissolved in 40 ml of acetonitrile were added at 0° C. The reaction mixture was stirred at room temperature for 24 hrs obtaining a clear solution, which was concentrated to dryness and the residue was triturated with diethyl ether. 56.8 g of a white solid were obtained.

M.p. 134°–136° C. (dec.).

Similarly were obtained:

1-azabicyclo [2.2.2]oct-3-yl chloroformate hydrochloride. M.p. 130°–132° C.

Endo-9-methyl-9-azabicyclo[3.3.1]non-3-yl-chloroformate hydrochloride. M.p. 117°–120° C.

EXAMPLE 2

2,3-Dihydro-2-oxo-1H-benzimidazole-1-carbonyl chloride

It was prepared by suspending 5 g of 2,3-dihydro-1H-benzimidazole-2-one in 200 ml of distilled tetrahydrofuran and by adding 13.5 ml of trichloromethylchloroformate. The reaction mixture was refluxed for 3 hrs until a clear solution was obtained. After cooling the separated solid was removed by filtration and after concentration to dryness of the mother liquors 6.5 g of the title compound were obtained.

M.p. 188°–190° C. (dec.).

EXAMPLE 3

N-(2-amino-5-nitrophenyl) (endo-8-methyl-8-azabicyclo [3.2.1]oct-3-yl-carbamate

Endo-8-methyl-8-azabicyclo[3.2.1]oct-3-yl chloroformate hydrochloride (7.85 g) was added portionwise, under stirring at room temperature, to a solution of 5 g of 4-nitro-1,2-phenylendiamine in pyridine (70 ml). The reaction mixture was stirred at the same temperature for 1 hr, evaporated to dryness, taken up in water and made acidic with HCl. The aqueous phase was washed with ethyl acetate and made basic with sodium hydroxide. A solid separated which was removed by filtration. 4.8 g of the title compound was obtained. M.p. 75°–77° C.

EXAMPLE 4

Endo-2-methyl-2-azabicyclo[2.2.2]octan-5-ol

The product was obtained according to R.F. Borne-J. Med. Chem. 16, 853–856 (1973). In that paper the compound was identified as "trans".

EXAMPLE 5

N-(2-aminophenyl) (endo-8-methyl-8-azabicyclo [3.2.1]oct-3-yl)carbamic acid ester a) To solution of 2-nitroaniline (25.0 g) in dry pyridine in dry pyridine (75 ml) endo-8-methyl-8-azabicyclo[3.2.1]oct-3-yl chloroformate hydrochloride (8.7 g) was added portionwise under stirring at room temperature. Once the initial exothermic reaction had subsided the reaction mixture was heated to 80° C. and stirred for 4 hrs. After cooling the pure N-(2-nitrophenyl) (endo-8-methyl-8-azabicyclo[3.2.1]oct-3-yl)carbamic acid ester, hydrochloride was recovered by filtration. 6.5 g. M.p.>250° C.

IR (cm$^{-1}$) nujol: 1720, 1605, 1590, 1520

Starting from the proper chlorofomate hydrochlorides and the proper 2-nitroaniline derivatives the following compounds were also obtained:

N-(4-methoxy-2-nitrophenyl)(endo-8-methyl-8-azabicyclo [3.2.1]oct-3-yl)carbamic acid ester, hydrochloride. M.p. 248°è–250° C.

N-(2-nitrophenyl)(1-azabicyclo[2.2.2]oct-3-yl)carbamic acid ester, hydrochloride. M.p.>250° C.

N-(2-nitrophenyl)(1-methylpiperidin-4-yl)carbamic acid ester. M.p. 87°–89° C.

N-(5-fluoro-2-nitrophenyl)(endo-8-methyl-8-azabicyclo [3.2.1]oct-3-yl)carbamic acid ester, hydrochloride. M.p. 257°–258° C.

N-(4-fluoro-2-nitrophenyl)(endo-8-methyl-8-azabicyclo [3.2.1]oct-3-yl)carbamic acid ester, hydrochloride. M.p. 255°–256° C.

N-(5-methoxy-2-nitrophenyl)(endo-8-methyl-8-azabicyclo [3.2.1]oct-3-yl)carbamic acid ester. M.p. 123°–124° C.

N-(2-nitrophenyl)(endo-8-phenylmethyl-8-azabicyclo [3.2.1]oct-3-yl)carbamic acid ester, hydrochloride M.p. 205°–207° C.

b) A solution of N-(2-nitrophenyl)(endo-8-methyl-8-azabicyclo[3.2.1]oct-oct-3-yl)carbamic acid ester, hydrochloride (6.5 g) in 70% aqueous ethanol (200 ml) was hydrogenated at room temperature and atmospheric pressure in the presence of 10% Pd/C (0.3 g). After the teoretical absorption the reaction mixture was filtered and concentrated to dryness. The residue was take up in acid water and the aqueous phase was washed with diethyl ether. The aqueous phase was then made basic and extracted with ethyl acetate; the organic extracts were dried over MgSO$_4$ and concentrated to dryness. 4.4 g of pure title compound were obtained from diisopropyl ether. M.p. 155°–157° C.

IR (cm$^{-1}$) nujol: 3420, 3260, 1680, 1605, 1590, 1540.

Similarly and using, according to the cases, an appropriate catalyst or general methods of chemical reduction, the following compounds were obtained:

N-(4-methoxy-2-aminophenyl)(endo-8-methyl-8-azabicyclo [3.2.1]oct-3-yl)carbamic acid ester. M.p. 118°–120° C.

N-(2-aminophenyl)(1-azabicyclo[2.2.2]oct-3-yl)carbamic acid ester. M.p. 165°–167° C.

N-(2-aminophenyl)(1-methylpiperidin-4-yl)carbamic acid ester. M.p. 153°–155° C.

N-(2-amino-5-fluorophenyl)(endo-8-methyl-8-azabicyclo [3.2.1]oct-3-yl)carbamic acid ester. M.p. 180°–181° C.

N-(2-amino-4-fluorophenyl)(endo-8-methyl-8-azabicyclo [3.2.1]oct-3-yl)carbamic acid ester. M.p. 171°–172° C.

N-(2-amino-5-methoxyphenyl)(endo-8-methyl-8-azabicyclo [3.2.1]oct-3-yl)carbamic acid ester. M.p. 144°–145° C.

N-(2-aminophenyl)(endo-8-phenylmethyl-8-azabicyclo [3.2.1]oct-3-yl)carbamic acid ester. M.p. 153°–155° C.

EXAMPLE 6

2,3-Dihydro-2-oxo-1H-benzimidazole-1-carboxylic acid (endo-8-methyl-8-azabicyclo[3.2.1]oct-3-yl)ester (Compound 1)

A solution of N-(2-aminophenyl)(endo-8-methyl-8-azabicyclo[3.2.1]oct-3-yl)carbamic acid ester (4.14 g) and triethylamine (2.5 ml) in dry methylene chloride (65 ml) was slowly added dropwise into a solution of trichloromethyl chloroformate (1.99 ml) in the same solvent (20 ml) at 5° C. under stirring. When the addition was over (60 min) the temperature was allowed to reach 25° C. while stirring was continued for another 60 min. Acidic water was then added and the organic phase was discarded; the aqueous phase was made basic and extracted with methylene chloride. After evaporation of the solvent the crude product was obtained and crystallized from acetonitrile 2.2 g. M.p. 191°–192° C.

MS (C.I.): 302 m/e [M+H]+
IR (cm$^{-1}$) nujol: 1760, 1720

| Analysis $C_{16}H_{19}N_3O_3$ | | | | | | |
|---|---|---|---|---|---|---|
| Found % | C | 63.40 | H | 6.42 | N | 13.76 |
| Calc. % | C | 63.77 | H | 6.36 | N | 13.95 |

The hydrochloride salt was also prepared M.p. 260°–261° C. (CH₃CN)

Similarly were prepared:
2,3-dihydro-2-oxo-1H-benzimidazole-1-carboxylic acid(1-azabicyclo[2.2.2]oct-3-yl)ester, hydrochloride (Compound 4)
M.p. 260° C.
MS (C.I.): 288 m/e [M+H]+
IR (cm$^{-1}$): 1760, 1720 broad

| Analysis $C_{15}H_{17}N_3O_3.HCl$ | | | | | | |
|---|---|---|---|---|---|---|
| Found % | C | 55.17 | H | 5.62 | N | 12.75 |
| Calc. % | C | 55.64 | H | 5.60 | N | 12.98 |

6-fluoro-2,3-dihydro-2-oxo-1H-benzimidazole-1-carboxylic acid (endo-8-methyl-8-azabicyclo[3.2.1]oct-3-yl)ester (Compound 10)
Hydrochloride. M.p. 261°–263° C.

| Analysis $C_{16}H_{18}FN_3O_3.HCl$ | | | | | | |
|---|---|---|---|---|---|---|
| Found % | C | 53.65 | H | 5.45 | N | 11.69 |

| Analysis $C_{16}H_{18}FN_3O_3.HCl$ | | | | | | |
|---|---|---|---|---|---|---|
| Calc. % | C | 54.00 | H | 5.38 | N | 11.81 |

5-fluoro-2,3-dihydro-2-oxo-1H-benzimidazole-1-carboxylic acid (endo-8-methyl-8-azabicyclo[3.2.1]oct-3-yl) ester (Compound 12)
Hydrochloride. M.p. 257°–258° C.

| Analysis $C_{16}H_{18}FN_3O_3.HCl$ | | | | | | |
|---|---|---|---|---|---|---|
| Found % | C | 53.89 | H | 5.41 | N | 11.71 |
| Calc. % | C | 54.00 | H | 5.38 | N | 11.81 |

6-methoxy-2,3-dihydro-2-oxo-1H-benzimidazole-1-carboxylic acid (endo-8-methyl-8-azabicyclo[3.2.1]oct-3-yl) ester (Compound 16)
Hydrochloride. M.p.>260° C.

| Analysis $C_{17}H_{21}N_3O_4.HCl$ | | | | | | |
|---|---|---|---|---|---|---|
| Found % | C | 54.97 | H | 6.09 | N | 11.21 |
| Calc. % | C | 55.51 | H | 6.03 | N | 11.42 |

By proceeding analogously the following intermediate was obtained:
2,3-dihydro-2-oxo-1H-benzimidazole-1-carboxylic acid (endo-8-phenylmethyl-8-azabicyclo[3.2.1]oct-3-yl) ester
M.p. 212°–214° C.

| Analysis $C_{22}H_{23}N_3O_3$ | | | | | | |
|---|---|---|---|---|---|---|
| Found % | C | 69.30 | H | 6.12 | N | 11.03 |
| Calc. % | C | 70.00 | H | 6.14 | N | 11.13 |

EXAMPLE 7

Compound 1

To a solution of 2,3-dihydro-1H-benzimidazole-2-one (0.9 g) in dry dimethylformamide (15 ml) 80% sodium hydride (0.4 g) was added at room temperature under stirring. Stirring was continued until hydrogen evolution stopped. Then the reaction mixture was cooled to 5° C. Endo-8-methyl-8-azabicyclo[3.2.1]oct-3-yl chloroformate hydrochloride (1.38 g) was added portionwise at 5° C. After 30 min the temperature was allowed to reach 25° C. and stirring was continued for further 60 min. The reaction mixture was evaporated to dryness then was taken up in acidic water and the aqueous phase was washed with ethyl acetate. The phase was made basic and extracted with methylene chloride. Evaporation of the solvent left a raw material which was purified by flash cromatography technique (eluent CH₂Cl₂/MeOH/32% NH₄OH 90:10:1) on Silicagel. 0.3 g M.p. 190°–191° C.
MS (C.I.): 302 m/e [M+H]+
IR (cm$^{-1}$) nujol: 1760, 1720

| Analysis $C_{16}H_{19}N_3O_3$ | | | | | | |
|---|---|---|---|---|---|---|
| Found % | C | 63.19 | H | 6.44 | N | 13.68 |
| Calc. % | C | 63.77 | H | 6.36 | N | 13.95 |

Analogously was obtained:

2,3-dihydro-2-oxo-1H-benzimidazole-1-carboxylic acid (endo-9-methyl-9-azabicyclo[3.3.1]non-3-yl) ester (Compound 19)

Citrate (freeze-dried). M.p. 96°–100° C.
MS (C.I.): 316 m/e [M+H]+

| Analysis C$_{17}$H$_{21}$N$_3$O$_3$.C$_6$H$_8$O$_7$ | | | | | | |
|---|---|---|---|---|---|---|
| Found % | C | 51.36 | H | 5.91 | N | 7.74 |
| Calc. % | C | 54.43 | H | 5.76 | N | 8.28 |

EXAMPLE 8

Compound 1

A solution of N-(2-aminophenyl)(endo-8-methyl-8-azabicyclo[3.2.1]oct-3-yl)carbamic acid ester (1.0 g) and carbonyldiimidazole (1.8 g) in benzene was heated to reflux for 1 hr. After cooling acidic water was added and the organic phase was discarded. The aqueous phase was made basic and extracted with methylene chloride. The organic phase was thoroughly washed with saturated NaCl solution, then dried over MgSO$_4$ and concentrated to dryness. Crystallization of the crude material from acetonitrile afforded the pure title compound (0.6 g).

M.p. 191°–192° C.

| Analysis C$_{16}$H$_{19}$N$_3$O$_3$ | | | | | | |
|---|---|---|---|---|---|---|
| Found % | C | 63.66 | H | 6.38 | N | 13.89 |
| Calc. % | C | 63.77 | H | 6.36 | N | 13.95 |

EXAMPLE 9

Compound 1

2,3-dihydro-2-oxo-1H-benzimidazole-1-carbonyl-chloride (2.15 g) was closely mixed with endo-8-methyl-8-azabicyclo[3.2.1]octan-3-ol (1.55 g) and the mixture was melted and let for 10 minutes at that temperature. After the residue was taken up in acidic water and washed with ethylacetate. The aqueous phase was made strongly basic and again extracted. The latter extracts were dried and evaporation of the solvent left the raw title compound which was crystallized from acetonitrile. 0.4. g. M.p. 190°–192° C.

| Analysis C$_{16}$H$_{19}$N$_3$O$_3$ | | | | | | |
|---|---|---|---|---|---|---|
| Found % | C | 63.45 | H | 6.41 | N | 13.81 |
| Calc. % | C | 63.77 | H | 6.36 | N | 13.95 |

Analogously was prepared:
2,3-dihydro-2-oxo-1H-benzimidazole-1-carboxylic acid (endo-2-methyl-2-azabicyclo[2.2.2]oct-5-yl) ester (Compound 24)

Citrate M.p. 73°–75° C.

| Analysis C$_{16}$H$_{19}$N$_3$O$_3$.C$_6$H$_8$O$_7$ | | | | | | |
|---|---|---|---|---|---|---|
| Found % | C | 52.96 | H | 5.64 | N | 8.39 |
| Calc. % | C | 53.55 | H | 5.52 | N | 8.52 |

EXAMPLE 10

3-methyl-2,3-dihydro-2-oxo-1H-benzimidazole-1-carboxylic acid (endo-8-methyl-8-azabicyclo[3.2.1]oct-3-yl) ester (Compound 25)

80% sodium hydride (0.04 g) was added portionwise to a solution of 2,3-dihydro-2-oxo-1H-benzimidazole-1-carboxylic acid (endo-8-methyl-8-azabicyclo[3.2.1]oct-3-yl ester (0.4 g) in dry DMF (10 ml). After hydrogen evolution had subsided methyl iodide (0.082 ml) was added and the reaction mixture was stirred at room temperature for 2 hrs. The solvent was removed under vacuum and the residue was taken up in methylene chloride and washed with water. The organic phase was dried over MgSO$_4$ and concentrated to dryness. Pure title compound was obtained by flash chromatography technique (eluent: methylene chloride/methanol/32% NH$_4$OH 90:10:1) on Silicagel. The oily base was transformed into the hydrochloride salt. 0.21 g M.p.>250° C.

MS (C.I.): 316 m/e [M+H]+

| Analysis C$_{17}$H$_{21}$N$_3$O$_3$ | | | | | | |
|---|---|---|---|---|---|---|
| Found % | C | 57.91 | H | 6.34 | N | 11.91 |
| Calc. % | C | 58.04 | H | 6.30 | N | 11.94 |

Analogously were prepared:
N-(endo-8-methyl-8-azabicyclo[3.2.1]oct-3-yl)-2,3-dihydro-3-ethyl-2-oxo-1H-benzimidazole-1-carboxamide (Compound 45)

Hydrochloride. M.p. 242°–244° C.

| Analysis C$_{18}$H$_{24}$N$_4$O$_2$.HCl | | | | | | |
|---|---|---|---|---|---|---|
| Found % | C | 58.35 | H | 7.06 | N | 15.01 |
| Calc. % | C | 59.25 | H | 6.91 | N | 15.36 |

N-(endo-8-methyl-8-azabicyclo[3.2.1]oct-3-yl)-2,3-dihydro-3-propyl-2-oxo-1H-benzimidazole-1-carboxamide (Compound 46)

Hydrochloride. M.p. 116°–119° C.

| Analysis C$_{19}$H$_{26}$N$_4$O$_2$.HCl | | | | | | |
|---|---|---|---|---|---|---|
| Found % | C | 59.54 | H | 7.23 | N | 14.44 |
| Calc. % | C | 60.23 | H | 7.18 | N | 14.79 |

N-(endo-8-methyl-8-azabicyclo[3.2.1]oct-3-yl)-2,3-dihydro-3-[1-(methyl)-ethyl]-2-oxo-1H-benzimidazole-1-carboxamide (Compound 47)

Hydrochloride. M.p. 117°–120° C.

| Analysis C$_{19}$H$_{26}$N$_4$O$_2$.HCl | | | | | | |
|---|---|---|---|---|---|---|
| Found % | C | 58.97 | H | 7.34 | N | 14.23 |
| Calc. % | C | 60.23 | H | 7.18 | N | 14.79 |

3-[1-(methyl)propyl]-2-3-dihydro-2-oxo-1H-benzimidazole-1-carboxylic acid (endo-8-methyl-8-azabicyclo[3.2.1]oct-3-yl) ester (Compound 48)

Hydrochloride. M.p. ~90° C. (freeze-dried)

| Analysis C$_{20}$H$_{27}$N$_3$O$_3$.HCl | | | | | | |
|---|---|---|---|---|---|---|
| Found % | C | 60.03 | H | 7.03 | N | 10.41 |

-continued

| Analysis C$_{20}$H$_{27}$N$_3$O$_3$.HCl | | | | | | |
|---|---|---|---|---|---|---|
| Calc. % | C | 60.98 | H | 7.16 | N | 10.67 |

N-(endo-8-methyl-8-azabicyclo[3.2.1]oct-3-yl)-2,3-dihydro-3-[2-(methyl)-propyl]-2-oxo-1H-benzimidazole-1-carboxamide (Compound 49)
Hydrochloride. M.p. 169°-170° C.

| Analysis C$_{20}$H$_{28}$N$_4$O$_2$.HCl | | | | | | |
|---|---|---|---|---|---|---|
| Found % | C | 60.83 | H | 7.37 | N | 14.36 |
| Calc. % | C | 61.14 | H | 7.44 | N | 14.26 |

N-(endo-8-methyl-8-azabicyclo[3.2.1]oct-3-yl)-2,3-dihydro-3-hexyl-2-oxo-1H-benzimidazole-1-carboxamide (Compound 50)
Hydrochloride. M.p. 214°-215° C.

| Analysis C$_{22}$H$_{32}$N$_4$O$_2$.HCl | | | | | | |
|---|---|---|---|---|---|---|
| Found % | C | 62.64 | H | 8.00 | N | 13.23 |
| Calc. % | C | 62.77 | H | 7.90 | N | 13.31 |

N-(endo-9-methyl-9-azabicyclo[3.3.1]non-3-yl)-2,3-dihydro-3-ethyl-2-oxo-1H-benzimidazole-1-carboxamide (Compound 51)
Hydrochloride. M.p. 259°-260° C.

| Analysis C$_{19}$H$_{26}$N$_4$O$_2$.HCl | | | | | | |
|---|---|---|---|---|---|---|
| Found % | C | 60.26 | H | 7.20 | N | 14.78 |
| Calc. % | C | 60.23 | H | 7.18 | N | 14.79 |

3-Ethyl-2,3-dihydro-2-oxo-1H-benzimidazole-1-carboxylic acid (endo-9-methyl-9-azabicyclo[3.3.1]non-3-yl) ester (Compound 52)
Hydrochloride. M.p. 239°-240° C.

| Analysis C$_{19}$H$_{25}$N$_3$O$_3$.HCl | | | | | | |
|---|---|---|---|---|---|---|
| Found % | C | 59.99 | H | 6.97 | N | 11.04 |
| Calc. % | C | 60.07 | H | 6.90 | N | 11.06 |

3-Methyl-2,3-dihydro-2-oxo-1H-benzimidazole-1-carboxylic acid (endo-9-methyl-9-azabicyclo[3.3.1]non-3-yl) ester (Compound 53)
Hydrochloride. M.p. 229°-230° C.

| Analysis C$_{18}$H$_{23}$N$_3$O$_3$.HCl | | | | | | |
|---|---|---|---|---|---|---|
| Found % | C | 58.33 | H | 6.68 | N | 11.03 |
| Calc. % | C | 59.09 | H | 6.61 | N | 11.49 |

3-Butyl-2,3-dihydro-2-oxo-1H-benzimidazole-1-carboxylic acid (endo-9-methyl-9-azabicyclo[3.3.1]non-3-yl) ester (Compound 54)
Hydrochloride. M.p.167°-168° C.

| Analysis C$_{21}$H$_{29}$N$_3$O$_3$.HCl | | | | | | |
|---|---|---|---|---|---|---|
| Found % | C | 61.26 | H | 7.52 | N | 9.93 |
| Calc. % | C | 61.83 | H | 7.41 | N | 10.30 |

N-(endo-8-methyl-8-azabicyclo[3.2.1]oct-3-yl)-2,3-dihydro-3-(2-propin-1-yl)-2-oxo-1H-benzimidazole-1-carboxamide (Compound 56)
Hydrochloride. M.p.256°-257° C.

| Analysis C$_{19}$H$_{22}$N$_4$O$_2$.HCl | | | | | | |
|---|---|---|---|---|---|---|
| Found % | C | 60.86 | H | 6.36 | N | 14.97 |
| Calc. % | C | 60.88 | H | 6.18 | N | 14.95 |

N-(endo-8-methyl-8-azabicyclo[3.2.1]oct-3-yl)-2,3-dihydro-3[3-(methyl)-but-2-en-1-yl]2-oxo-1H-benzimidazole-1-carboxamide (Compound 57)
Hydrochloride. M.p. 196°-198° C.

| Analysis C$_{21}$H$_{28}$N$_4$O$_2$.HCl | | | | | | |
|---|---|---|---|---|---|---|
| Found % | C | 61.53 | H | 7.32 | N | 13.81 |
| Calc. % | C | 62.29 | H | 7.22 | N | 13.84 |

3-[1-Methyl)-ethyl]-2,3-dihydro-2-oxo-1H-benzimidazole-1-carboxylic acid (endo-8-methyl-8-azabicyclo[3.2.1]oct-3-yl) ester (Compound 59)
Hydrochloride. M.p. 179°-180° C.

| Analysis C$_{19}$H$_{25}$N$_3$O$_3$.HCl | | | | | | |
|---|---|---|---|---|---|---|
| Found % | C | 59.30 | H | 6.95 | N | 10.94 |
| Calc. % | C | 60.07 | H | 6.90 | N | 11.06 |

3-Ethyl-2,3-dihydro-2-oxo-1H-benzimidazole-1-carboxylic acid (endo-8-methyl-8-azabicyclo[3.2.1]oct-3-yl) ester (Compound 60)
Hydrochloride. M.p. 250° C. (dec.)

| Analysis C$_{18}$H$_{23}$N$_3$O$_3$.HCl | | | | | | |
|---|---|---|---|---|---|---|
| Found % | C | 58.25 | H | 6.53 | N | 11.14 |
| Calc. % | C | 59.09 | H | 6.61 | N | 11.48 |

EXAMPLE 11

Compound 25

A suspension of 3-methyl-2,3-dihydro-1H-benzimidazole-2-one (1.5 g) and trichloromethylchloroformate (2.43 ml) in dry o-dichlorobenzene (150 ml) was stirred overnight at 80° C. After cooling to 10° C. the reactive intermediate was afforded by filtration. This compound was added to a solution of endo-8-methyl-8-azabicyclo[3.2.1]octran-3-ol (1.41 g) in dry pyridine (20 ml) at room temperature under stirring and, after the addition was over, the reaction mixture was stirred for 2 hrs at 80° C. After evaporation of the solvent the usual work-up afforded 0.7 g of the pure title compound as hydrochloride salt.
M.p.>250° C.
MS (C.I.): 316 m/e [M+H]+

| Analysis C$_{17}$H$_{21}$N$_3$O$_3$.HCl | | | | | | |
|---|---|---|---|---|---|---|
| Found % | C | 57.85 | H | 6.36 | N | 11.83 |
| Calc. % | C | 58.04 | H | 6.30 | N | 11.94 |

EXAMPLE 12

N-(endo-8-methyl-8-azabicyclo[3.2.1]oct-3-yl)-2,3-dihydro-2-oxo-1H-benzimidazole-1-carboxamide (Compound 26)

2,3-Dihydro-2-oxo-1H-benzimidazole-1-carbonyl chloride (1.5 g) was dissolved in tetrahydrofurane (40 ml) and to that solution a solution of endo-8-methyl-8-azabicyclo[3.2.1]octan-3-amine, dissolved in tetrahydrofurane (5 ml), was added dropwise at room temperature. When the addition was over a solid separated and the reaction mixture was stirred for 30 minutes, concentrated to dryness and taken up in diluted HCl. The aqueous phase was washed with ethyl acetate, made basic with a saturated sodium carbonate and again extracted. The latter organic layers were concentrated to dryness giving 0.7 g of the crude product. After crystallization from acetonitrile 0.17 g of the pure product were obtained.

M.p. 205°–207° C.
MS (C.I.): 301 m/e [M+H]+
IR (cm$^{-1}$): 1730, 1690

| Analysis $C_{16}H_{20}N_4O_2$ | | | | | | | |
|---|---|---|---|---|---|---|---|
| Found % | C | 62.83 | H | 6.75 | N | 18.01 |
| Calc. % | C | 63.98 | H | 6.71 | N | 18.65 |

Similarly were prepared:

N-(endo-9-methyl-9-azabicyclo[3.3.1]non-3-yl)-2,3-dihydro-2-oxo-1H-benzimidazole-1-carboxamide (Compound 27)
Hydrochloride. M.p. 269°–270° C.
MS (C.I.): 315 m/e [M+H]+

| Analysis $C_{17}H_{22}N_4O_2.HCl$ | | | | | | | |
|---|---|---|---|---|---|---|---|
| Found % | C | 58.40 | H | 6.62 | N | 15.91 |
| Calc. % | C | 58.19 | H | 6.61 | N | 15.97 |

N-(1-azabicyclo[2.2.2]oct-3-yl)-2,3-dihydro-2-oxo-1H-benzimidazole-1-carboxamide (Compound 28)
M.p. 196°–198° C.
MS (C.I.): 287 m/e [M+H]+

| Analysis $C_{15}H_{18}N_4O_2$ | | | | | | | |
|---|---|---|---|---|---|---|---|
| Found % | C | 62.34 | H | 6.32 | N | 19.34 |
| Calc. % | C | 62.92 | H | 6.34 | N | 19.57 |

N-(endo-1-azabicyclo[3.3.1]non-4-yl)-2,3-dihydro-2-oxo-1H-benzimidazole-1-carboxamide (Compound 29)
M.p. 245°–248° C.
MS (C.I.): 301 m/e [M+H]+

| Analysis $C_{16}H_{20}N_4O_2$ | | | | | | | |
|---|---|---|---|---|---|---|---|
| Found % | C | 64.18 | H | 6.80 | N | 18.58 |
| Calc. % | C | 63.98 | H | 6.71 | N | 18.65 |

N-(1-methylpiperidin-4-yl)-2,3-dihydro-2-oxo-1H-benzimidazole-1-carboxamide (Compound 30)
M.p. 194°–197° C.
MS (C.I.): 275 m/e [M+H]+

| Analysis $C_{14}H_{18}N_4O_2$ | | | | | | | |
|---|---|---|---|---|---|---|---|
| Found % | C | 61.18 | H | 6.80 | N | 20.34 |
| Calc. % | C | 61.30 | H | 6.61 | N | 20.42 |

N-(endo-9-methyl-9-azabicyclo[3.3.1]non-3-yl)-3-methyl-2,3-dihydro-2-oxo-1H-benzimidazole-1-carboxamide (Compound 31)
M.p. 175°–176° C.
MS (C.I.): 329 m/e [M+H]+

| Analysis $C_{18}H_{24}N_4O_2$ | | | | | | | |
|---|---|---|---|---|---|---|---|
| Found % | C | 65.39 | H | 7.32 | N | 16.92 |
| Calc. % | C | 65.83 | H | 7.36 | N | 17.06 |

N-(endo-8-methyl-8-azabicyclo[3.2.1]oct-3-yl)-3-methyl-2,3-dihydro-2-oxo-1H-benzimidazole-1-carboxamide (Compound 32)
Hydrochloride. M.p. 269°–270° C.
MS (C.I.): 315 m/e [M+H]+

| Analysis $C_{17}H_{22}N_4O_2.HCl$ | | | | | | | |
|---|---|---|---|---|---|---|---|
| Found % | C | 58.14 | H | 6.49 | N | 16.01 |
| Calc. % | C | 58.19 | H | 6.61 | N | 15.97 |

By proceeding analogously the following intermediate was obtained:

N-(endo-8-phenylmethyl-8-azabicyclo[3.2.1]oct-3-yl)-2,3-dihydro-2-oxo-1H-benzimidazole-1-carboxamide
M.p. 221°–224° C.

| Analysis $C_{22}H_{24}N_4O_2$ | | | | | | | |
|---|---|---|---|---|---|---|---|
| Found % | C | 70.02 | H | 6.41 | N | 14.69 |
| Calc. % | C | 70.19 | H | 6.43 | N | 14.88 |

EXAMPLE 13

N-(endo-9-methyl-9-azabicyclo[3.3.1]non-3-yl)-2,3-dihydro-2-oxo-1H-benzimidazole-1-carboxamide (Compound 27)

A solution of N-(endo-9-methyl-9-azabicyclo[3.3.1]-non-3-yl)N-[(2,4-dimethoxyphenyl)methyl]-2,3-dihydro-2-oxo-1H-benzimidazole-1-carboxamide (1.0 g) and anisole (0.6 g) in trifluoroacetic acid (10 ml) was stirred at room temperature for 12 hrs. The reaction mixture was then concentrated to dryness and the residue oil was purified by flash-chromatography on silica-gel: eluent methylene chloride-methanol-32% ammonium hydroxide 80:20:2. 0.12 g of the title compound were obtained.

M.p. 180°–182° C.

| Analysis $C_{17}H_{22}N_4O_2$ | | | | | | | |
|---|---|---|---|---|---|---|---|
| Found % | C | 64.83 | H | 7.02 | N | 17.75 |
| Calc. % | C | 64.95 | H | 7.05 | N | 17.82 |

Analogously and starting from the appropriate precursor was also obtained:

N-(endo-9-methyl-9-azabicyclo[3.3.1]non-3-yl)-3-methyl-2,3-dihydro-2-oxo-1H-benzimidazole-1-carboxamide (Compound 31)
M.p. 175°–176° C.

| Analysis $C_{18}H_{24}N_4O_2$ | | | | | | |
|---|---|---|---|---|---|---|
| Found % | C | 65.12 | H | 7.38 | N | 16.94 |
| Calc. % | C | 65.83 | H | 7.36 | N | 17.06 |

EXAMPLE 14

2,3-dihydro-2-oxo-1H-benzimidazole-1-carboxylic acid (endo-8-methyl-8-azabicyclo[3.2.1]oct-3-yl) ester, methobromide (Compound 37)

A solution of 2,3-dihydro-2-oxo-1H-benzimidazole-1-carboxylic acid (endo-8-methyl-8-azabicyclo[3.2.1]oct-3-yl) ester (0.5 g) in acetone (60 ml) was added in 40 minutes to a mixture of acetone (20 ml) and methylbromide [2M solution in diethyl ether (20 ml)], cooled at 5° C. The resulting mixture was left overnight at room temperature. The crude product separated as a solid and was recovered by filtration. After crystallization from ethanol 0.2 g of the pure product were obtained. M.p. >260° C.

| Analysis $C_{17}H_{22}BrN_3O_3$ | | | | | | |
|---|---|---|---|---|---|---|
| Found % | C | 51.02 | H | 5.65 | N | 10.33 |
| Calc. % | C | 51.48 | H | 5.60 | N | 10.60 |

EXAMPLE 15

2,3-dihydro-2-oxo-1H-benzimidazole-1-carboxylic acid (endo-8-azabicyclo[3.2.1]oct-3-yl) ester (Compound 38)

A suspension of 2,3-dihydro-2-oxo-1H-benzimidazole-1-carbonyl chloride (1.3 g) and endo-8-azabicyclo[3.2.1]octan-3-ol hydrochloride (1.0 g) in o-dichloro-benzene (5 ml) was heated at 180° C. for 1 hour under stirring. The reaction mixture was then allowed to cool and the solvent was removed by filtration. The crude product so obtained was washed with a little ethanol and crystallized from ethanol. 1.1 g of the desired product was obtained. M.p. >260° C.

M.S. (C.I.): 288 m/e [M+H]+

| Analysis $C_{15}H_{17}N_3O_3 \cdot HCl$ | | | | | | |
|---|---|---|---|---|---|---|
| Found % | C | 55.15 | H | 5.61 | N | 12.70 |
| Calc. % | C | 55.64 | H | 5.60 | N | 12.98 |

EXAMPLE 16

N-(endo-8-azabicyclo[3.2.1]oct-3-yl)-2,3-dihydro-2-oxo-1H-benzimidazole-1-carboxamide (Compound 39)

A suspension of N-(endo-8-phenylmethyl-8-azabicyclo[3.2.1]oct-3-yl)-2,3-dihydro-2-oxo-1H-benzimidazole-1-carboxamide (1.0 g) in 1:1 aqueous ethanol (50 ml) was hydrogenated at room temperature and 10 atm. pressure in the presence of 10% Pd/C. After the usual workup 0.6 g of the title compound were obtained.

Hydrochloride. M.p. >250° C.

| Analysis $C_{15}H_{18}N_4O_2 \cdot HCl$ | | | | | | |
|---|---|---|---|---|---|---|
| Found % | C | 55.64 | H | 5.96 | N | 17.21 |
| Calc. % | C | 55.81 | H | 5.93 | N | 17.36 |

EXAMPLE 17

2,3-dihydro-2-oxo-1H-benzimidazole-1-carboxylic acid (endo-8-iminomethyl-8-azabicyclo[3.2.1]oct-3-yl) ester (Compound 41)

Ethyl formimidate hydrochloride (0.5 g) was added portionwise to a solution of 2,3-dihydro-2-oxo-1H-benzimidazole-1-carboxylic acid (endo-8-azabicyclo[3.2.1]oct-3-yl) ester (1.0 g) in ethanol (40 ml). The solution was stirred at room temperature for 1 hour, and the solid so separated was recovered by filtration. Yield 0.4 g. Hydrochloride. M.p. 210°-212° C.

MS (C.I.): 315 m/e [M+H]+

| Analysis $C_{16}H_{18}N_4O_3 \cdot HCl$ | | | | | | |
|---|---|---|---|---|---|---|
| Found % | C | 53.96 | H | 5.51 | N | 15.62 |
| Calc. % | C | 54.78 | H | 5.46 | N | 15.97 |

Analogously was obtained:
N-(endo-8-iminomethyl-8-azabicyclo[3.2.1]non-3-yl)-2,3-dihydro-2-oxo-1H-benzimidazole-1-carboxamide (Compound 42)

Hydrochloride (freeze-dried). M.p. 65°-70° C.:
MS (C.I.): 314 m/e [M+H]+

| Analysis $C_{16}H_{19}N_5O_2 \cdot HCl$ | | | | | | |
|---|---|---|---|---|---|---|
| Found % | C | 53.86 | H | 5.84 | N | 19.87 |
| Calc. % | C | 54.34 | H | 5.76 | N | 20.02 |

EXAMPLE 18

2,3-dihydro-2-oxo-1H-benzimidazole-1-carboxylic acid (endo-8-amidino-8-azabicyclo[3.2.1]oct-3-yl) ester (Compound 44)

Cyanamide (0.26 g) was added under stirring to a suspension of 2,3-dihydro-2-oxo-1H-benzimidazole-1-carboxylic acid (endo-8-azabicyclo[3.2.1]oct-3-yl) ester, hydrochloride in 0.5 ml of water. The homogenized reaction mixture was heated to 130° C. and kept under stirring at that temperature for 2 hours. After cooling the crude product was purified by flash-chromatography on silica-gel: elent n-propanol-acetic acid-water 90:10:10. After freeze-drying 0.3 g of the pure product were obtained.

M.p. 70°-75° C.
MS (C.I.): 330 m/e [M+H]+

| Analysis $C_{16}H_{19}N_5O_3 \cdot HCl$ | | | | | | |
|---|---|---|---|---|---|---|
| Found % | C | 51.73 | H | 5.45 | N | 19.17 |
| Calc. % | C | 52.53 | H | 5.51 | N | 19.14 |

The following not limitative examples of pharmaceutical compositions according to the invention are reported:

EXAMPLE 19

| Tablets | |
|---|---|
| active ingredient | 250 mg |
| lactose | 270 mg |
| corn starch | 76 mg |
| magnesium stearate | 4 mg |

Method of preparation: The active ingredient, lactose and corn starch were mixed and homogeneously moistened with water. After screening of the moist mass and drying in a tray drier, the mixture was again passed throught a screen and magnesium stearate was added. Then the mixture was pressed into tablets weighing 600 mg each. Each tablet contains 250 mg of active ingredient.

EXAMPLE 20

| Capsules | |
|---|---|
| active ingredient | 250 mg |
| lactose | 148 mg |
| magnesium stearate | 2 mg |

Method of preparation: The active ingredient was mixed with auxiliary products, and the mixture was passed through a screen and mixed homogeneously in a suitable device. The resulting mixture was filled into hard gelatine capsules (400 mg per capsule); each capsule contains 250 mg of active ingredient.

EXAMPLE 21

| Ampoules | |
|---|---|
| active ingredient | 50 mg |
| Sodium chloride | 10 mg |

Method of preparation: the active ingredient and sodium chloride were dissolved in a appropriate amount of water for injection. The resulting solution was filtered and filled into ampoules under sterile conditions. Each ampoule contains 50 mg of active ingredient.

EXAMPLE 22

| Suppositories | |
|---|---|
| active ingredient | 250 mg |
| semisynthetic glicerides of fatty acids | 950 mg |

Method of preparation: The semisynthetic glicerides of fatty acids were melted and the active ingredient was added while stirring homogeneously. After cooling at a proper temperature the mass was poured into performed moulds for suppositories weighing 1200 mg each. Each suppository contains 250 mg of active ingredient.

EXAMPLE 23

| Oral drops | |
|---|---|
| active ingredient | 50 mg |
| sorbitol | 350 mg |
| propylene glycol | 100 mg |
| citric acid | 1 mg |
| sodium citrate | 3 mg |
| demineralized water q.s. | 1 ml |

Method of preparation: The active ingredient, citric acid and sodium citrate were dissolved in a mixture of a proper amount of water and propylene glycol. Then sorbitol was added and the final solution was filtered. The solution contains 5% of active ingredient and is administered by using a proper dropper.

What is claimed is:

1. A compound of the formula (I)

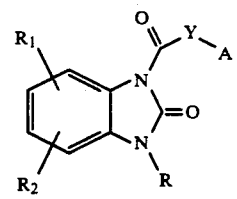

(I)

wherein,

R is hydrogen, $C_{1-6}$ alkyl, $C_{2-6}$ alkenyl, or $C_{2-6}$ alkynyl;

$R_1$ is hydrogen;

$R_2$ is hydrogen, halogen, or $C_{1-6}$ alkoxy;

Y is oxygen or N—$R_3$, in which $R_3$ is hydrogen; and,

A is a group of the formula

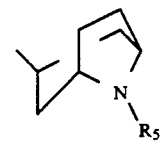

wherein $R_5$ is hydrogen, $C_{1-6}$ alkyl, or $R_5$ is a group of the formula —$CR_6$=N—$R_7$, wherein $R_6$ is hydrogen, $C_{1-4}$ alkyl or amino and $R_7$ is hydrogen or $C_{1-6}$ alkyl;

or a pharmaceutically acceptable acid addition salt thereof.

2. The salt of a compound according to claim 1, wherein the pharmaceutically acceptable acid used to form the salt is selected from the group consisting of hydrochloric, hydrobromic, sulphuric, acetic, citric or tartaric acid.

3. A compound of formula (I) according to claim 1, wherein A is endo-8-methyl-8-azabicyclo-[3.2.1]oct-3-yl, $R_1$ and $R_2$ are H, R is H, $C_{1-6}$ alkyl, $C_{2-6}$ alkenyl or $C_{2-6}$ alkynyl and Y is oxygen or NH.

4. N-(endo-8-methyl-8-azabicyclo[3.2.1]oct-3-yl)-2,3-dihydro-2-oxo-1H-benzimidazole-1-carboxamide or a pharmaceutically acceptable salt thereof.

5. N-(endo-8-methyl-8-azabicyclo[3.2.1]oct-3-yl)-3-methyl-2,3-dihydro-2-oxo-1H-benzimidazole-1-carboxamide or a pharmaceutically acceptable salt thereof.

6. N-(endo-8-methyl-8-azabicyclo[3.2.1]oct-3-yl)-2,3-dihydro-3-ethyl-2-oxo-1H-benzimidazole-1-carboxamide or a pharmaceutically acceptable salt thereof.

7. 3-Ethyl-2,3-dihydro-2-oxo-1H-benzimidazole-1-carboxylic acid (endo-8-methyl-8-azabicyclo[3.2.1]oct-3-yl) ester or a pharmaceutically acceptable salt thereof.

8. A pharmaceutical composition comprising as active ingredient at least one compound of formula (I) according to claim 1 or pharmaceutically acceptable acid addition salt thereof in association with pharmaceutical carriers or exicipients.

9. A method for treating a warm-blooded animal suffering from chemotherapy or radiation induced nausea or emesis, which method comprises administering to said animal a therapeutically effective amount of a compound of formula I, as set forth in claim 1.

* * * * *